(12) United States Patent
Knowles et al.

(10) Patent No.: US 8,633,248 B2
(45) Date of Patent: Jan. 21, 2014

(54) PARENTERAL SELENOMETHIONINE FOR PRODUCTION OF SELENIUM-RICH FOODS

(75) Inventors: Scott Oliver Knowles, Palmerston North (NZ); Neville Donovan Grace, Palmerston North (NZ)

(73) Assignee: AgResearch Limited, Hamilton (NZ)

( * ) Notice: Subject to any disclaimer, the term of this patent is extended or adjusted under 35 U.S.C. 154(b) by 789 days.

(21) Appl. No.: 11/993,798

(22) PCT Filed: Jun. 27, 2006

(86) PCT No.: PCT/NZ2006/000164
§ 371 (c)(1),
(2), (4) Date: Feb. 23, 2010

(87) PCT Pub. No.: WO2007/001194
PCT Pub. Date: Jan. 4, 2007

(65) Prior Publication Data
US 2011/0212243 A1    Sep. 1, 2011

(30) Foreign Application Priority Data
Jun. 27, 2005  (NZ) ........................................ 540958

(51) Int. Cl.
*A61K 31/195* (2006.01)

(52) U.S. Cl.
USPC ............ 514/561; 424/400; 424/423; 424/702

(58) Field of Classification Search
USPC ....................................................... 514/561
See application file for complete search history.

(56) References Cited

U.S. PATENT DOCUMENTS

| 4,326,523 | A | 4/1982 | Wolfrom et al. |
| 4,865,840 | A | 9/1989 | Burke et al. |
| 5,827,886 | A | 10/1998 | Hersh |
| 5,919,820 | A | 7/1999 | Moesgaard |
| 6,573,299 | B1 | 6/2003 | Petrus |
| 7,241,456 | B2 * | 7/2007 | Vromen ........................ 424/449 |

FOREIGN PATENT DOCUMENTS

| CN | 1094899 | 11/1994 |
| CN | 1217153 | 5/1999 |
| CN | 1439284 | 9/2003 |
| CN | 1452883 | 11/2003 |
| CN | 1452884 | 11/2003 |
| EP | 440341 B1 | 8/1991 |
| EP | 9131155 B1 | 3/2002 |
| RU | 2222192 | 3/2002 |
| TW | 565432 | 12/2003 |
| WO | WO 99/00106 | 1/1999 |
| WO | WO 2004/107881 | 12/2004 |
| WO | WO 2005/120457 | 12/2005 |

OTHER PUBLICATIONS

Bailey's—Viscosity of fats & oils—p. 98, 1964.*

(Continued)

*Primary Examiner* — Neil Levy
(74) *Attorney, Agent, or Firm* — Knobbe Martens Olson & Bear LLP

(57) ABSTRACT

A formulation for parenteral administration which includes selenomethionine and at least one oil-based vehicle. The formulation is used for elevating the selenium levels in the blood, milk and/or meat of an animal. These products (i.e. milk and meat) and the formulation itself are used to meet the selenium nutritional requirement for growth and health in a selenium deficient animal.

12 Claims, 9 Drawing Sheets

(56) References Cited

OTHER PUBLICATIONS

Jaskowsky et al—effect of Selenium or Vitamin E—Med.Weter. (46, No. 5, 148-150, 1990 Vetu Abstract# 1991-60550.*

Smith, G.M. and Allen, J.G., "Effectiveness of α-tocopherol and selenium supplements in preventing lupinosis-associated myopathy in sheep", *Australian Veterinary Journal*, (1997) 75(5):341.

Van Rij, et al., "Selenium Supplementation in Total Parenteral Nutrition", *Journal of Parenteral and Enteral Nutrition*, (1981) 5(2): 120-124.

Van Rij, et al., "Selenium deficiency in total parenteral nutrition", *The American Journal of Clinical Nutrition*, (1979) 32:2076-2085.

International Search Report, dated Nov. 3, 2006, issued in PCT/NZ2006/000164.

Grace, et al., "Influence of Se status on mild Se concentrations in dairy cows" *NZ J. Of Agricultural Research* (1997) 40: 75-78.

Knowles, et al., "Adding Nutritional Value to Meat and Milk from Pasture-fed Livestock" *NZ Veterinary J.* (2004) 52(6): 342-351.

Knowles, et al., "Significance of amount and form of dietary selenium on blood, milk, and casein selenium concentrations in grazing cows" *J. Of Dairy Science* (1999) 82: 429-437.

Judson, et al., "Long-Acting Selenium Treatments for Sheep" *Australian Veterinary Journal*, (1991) 68(8): 263-265.

Prasad, et al., "Influence of Different Sources of Injected Selenium on Certain Enzymes Glutathione and Adenosylmethionine Concentration in Buffalo Bubalus-Bubalis Calves" *British J. Nutrition*, (1991) 66(2): 261-268.

* cited by examiner

PARENTERAL SELENOMETHIONINE FOR PRODUCTION OF SELENIUM-RICH FOODS

RELATED APPLICATIONS

This application is a U.S. National Phase of International Application No. PCT/NZ2006/00164, filed Jun. 27, 2006, designating the U.S. and published on Jan. 4, 2007, as WO 2007/001194, which claims priority to New Zealand Patent Application No. 540958, filed on Jun. 27, 2005. The content of these applications are incorporated herein by reference in there entireties.

TECHNICAL FIELD

The invention relates to parenteral selenomethionine for production of selenium-rich foods. More specifically, the invention relates to a formulation containing selenomethionine and methods of use of that formulation to markedly increase the concentration of selenium in milk and/or meat produced and obtained from an animal.

BACKGROUND ART

Nutritional Roles and Value of Dietary Selenium

Informed consumers increasingly demand foods with benefits beyond simply nourishment, matched to lifestyles, individual preferences and to meet specific dietary requirements. This has spurred interest in foods containing high levels of vitamins and minerals. Nutritional modification to make such foods may be achieved several ways, but preferably by making desirable changes on-farm to directly improve the food without subsequent manipulations.

One mineral of interest is selenium, a trace element essential to growth and health in humans and animals generally. In the body, selenium is incorporated into proteins to make selenoproteins, which are active in cell detoxification, redox cycling, and antioxidant defence against cellular damage from free radicals. Free radicals are natural by-products of oxygen metabolism that contribute to the development of chronic diseases such as cancer and heart disease. Other selenoproteins regulate thyroid function and play a role in the immune system. Except in extreme cases, selenium deficiency does not by itself cause illness. Rather, it can make the body more susceptible to illnesses caused by other nutritional, biochemical or infectious stresses.

As for all essential minerals, diet is the source of selenium intake. Criteria in New Zealand and elsewhere define the selenium Dietary Reference Intake (RDI) or Recommended Daily Allowance (RDA) for healthy consumers of various ages. New Zealand and Australian RDIs were set by the Australian National Health and Medical Research Council, and currently are:

| | Population sub-group | | | | | |
|---|---|---|---|---|---|---|
| | adult men | adult women | boys | girls | toddlers | infants |
| Selenium RDI (µg/day) | 70 | 60-75 | 70 | 60 | 25 | 10-15 |

It should be appreciated by those skilled in the art that different countries have differences in RDI/RDA levels and the information above is provided by way of example only.

The selenium nutrition status of New Zealanders tends to be below World Health Organisation recommendations, as a consequence of the country's geology that determines mineral content of soil, which affects mineral uptake by crops and ultimately selenium content of locally grown foods. In the UK, recent changes in farming and import practices have also caused a drop in the selenium nutrition status of the general population.

People consuming a balanced and ample diet can usually meet their minimum intake requirement. However old habits, dieting or cultural practices that restrict variety of food choice can severely limit access to good selenium sources. Thus many consumers are looking for ways to boost their intake of selenium with nutritional supplements, often via pills but increasingly by eating nutrient-enhanced foods.

Meat and milk from New Zealand livestock naturally contains selenium, albeit at low concentrations which reflect composition of the grazing diets. Usual levels are 50 µg selenium/kg (range 30-85 µg/kg) in fresh lean beef or lamb[1], and 2-11 µg selenium/liter in whole milk[2]. The contribution made to a person's daily selenium requirement by eating a 100 g or 100 ml serving of "typical" meat or milk would be 1-6% and 1-20% for adults and toddlers, respectively. Obviously, higher concentrations of selenium would increase the benefit derived from 100 g or smaller food servings.

[1] West J. Compilation of nutritional data for New Zealand beef and lamb in domestic and export trade. Project 96MZ 64/4.3. New Zealand Meat Research and Development Council, Wellington, NZ, 1996. Unpublished report.

[2] Grace N D, Ankenbauer K, Alexander A M, Marchant R M. Relationship between blood selenium concentration or glutathione peroxidase activity, and milk selenium concentrations in New Zealand dairy cows. NZ Veterinary Journal 49:24-28, 2001.

In these foods (and in staple grains as well) selenium exists primarily as the organic chemical form selenomethionine, an analogue of the amino acid methionine. Selenomethionine can be incorporated into body proteins in place of methionine, and in this way serves as selenium storage in organs and tissues. Selenomethionine derived from foods is considered to have high bioavailability, in that it is well absorbed and utilised.

Improving Food Nutrition by Enriching Selenium Content

Enhanced foods can be produced by adding a nutrient such as selenium exogenously i.e. at the factory after harvest, or endogenously by causing extra selenium to be grown into the food prior to harvest or slaughter. The advantage of the latter is that selenium is incorporated into the food in its natural chemical form, is delivered to the consumer in an unadulterated way, and post-harvest processing or concentrating steps are avoided.

One method known to endogenously enrich the selenium content of milk from ruminants is by adding selenium or selenomethionine to the animal feed, as described for example in the Patent abstracts TW0565432B, CN1094899A and CN1217153A. The feed additive may also contain sodium selenite and sodium selenate, two inorganic forms of selenium salts. Examples of sodium selenite feed supplements are described in at least the abstracts of Chinese Patent No. CN1452884A, CN1439284A and CN1452883A.

An alternative method of increasing selenium levels in the animal and consequently in the meat or milk produced is to administer the selenium supplement by subcutaneous or intramuscular injection. Parenteral administration, which refers to the form being taken into the body in a manner other than through the digestive tract, has several distinct advantages over supplemented feed sources, as for example:

Treatment by injection is suitable for livestock that are primarily grazed on open pastures and not normally fed any supplements at all (e.g. in New Zealand).

The cost of producing and administering an injection formulation may be less than the cost of producing and feeding-out supplemented feeds;

The amount of selenium administered can be controlled accurately from an injection but is less certain from oral feeds due to variations in feed manufacture and amounts eaten by different animals;

Where only selected members of a herd are to be dosed with selenium, injection provides easier handling than oral feeds as treated animals do not need to be separated or their food regulated in any different way to other animals.

Dose quantities of selenium via injection are lesser, as selenium is not lost due to feed waste and poor absorption by the animal. This reduces the amount of selenium lost to the ground and potentially leeched into water supplies, and so gains advantage where environmental restrictions are in place.

Many injectable selenium supplements are on the market but none contain selenomethionine. Among these is Novartis Deposel®, a fluid formulation of micronised particles of barium selenate (an inorganic selenium salt) that is injected subcutaneously into livestock animals and provides a long lasting reservoir of selenium at the site of injection. Deposel® is registered for use in sheep and cattle to treat and prevent selenium deficiency. Its purpose is animal health maintenance with no claims for effect on selenium content in meat or milk.

At least 15 other injectable selenium supplements are registered in New Zealand as "parenteral nutrients". All are animal health remedies containing inorganic sodium selenite or sodium selenate, and none claim to affect meat or milk composition. The abstract of Russian Patent No. RU2222192C2 describes an intramuscular injection method of sodium selenite used to increase the volume of milk production, however no description is made of altered selenium levels in the milk produced.

The inventors have tested injectable formulations of barium selenate and sodium selenate in livestock and found that the animals' selenium status (i.e. the concentration of selenium in blood) is increased by treatment, but little selenium carries-through into the animals' milk or meat. Those food products are not sufficiently enriched to be used directly as a functional or enhanced food for human consumption without further processing such as concentrating steps. In one study completed by the inventors[1], a single subcutaneous injection of barium selenate was used to increase animal selenium blood status. The treatment raised the selenium concentration of milk over an entire lactation, but only by 2-fold (from 6 to 11 µg selenium/liter of milk).

[1] Grace N D, Lee J, Mills A R, Death A F. Influence of Se status on milk Se concentrations in dairy cows. NZ Journal of Agricultural Research 40:75-78, 1997.

In a second publication[2], methods for altering the amount of selenium in animal products are identified that include variation of pasture selenium intake (feed manipulation) or use of long-acting animal injections or use of oral ruminal boluses. The article also noted the use of an injection containing distinct chemical forms of organic selenium to enrich the selenium content of meat. The formulation(s) used to achieve that increase in meat selenium content was not described.

[2] Knowles SO et al. Adding Nutritional Value to Meat and Milk from Pasture-fed Livestock. NZ Veterinary Journal 52:342-351, 2004.

As parenteral administration of selenium to livestock has distinct advantages over supplemented feed sources (see bullet points above), it would therefore be advantageous to have an injectable formulation and suitable methods for its administration that could be used to significantly increase the concentration of selenium in milk or meat for the use and benefit of human consumers, for example, as a boost to consumers' dietary intake.

It is an object of the present invention to address the foregoing problems or at least to provide the public with a useful choice.

All references, including any patents or patent applications cited in this specification are hereby incorporated by reference. No admission is made that any reference constitutes prior art. The discussion of the references states what their authors assert, and the applicants reserve the right to challenge the accuracy and pertinency of the cited documents. It will be clearly understood that, although a number of prior art publications are referred to herein, this reference does not constitute an admission that any of these documents form part of the common general knowledge in the art, in New Zealand or in any other country.

It is acknowledged that the term 'comprise' may, under varying jurisdictions, be attributed with either an exclusive or an inclusive meaning. For the purpose of this specification, and unless otherwise noted, the term 'comprise' shall have an inclusive meaning—i.e. that it will be taken to mean an inclusion of not only the listed components it directly references, but also other non-specified components or elements. This rationale will also be used when the term 'comprised' or 'comprising' is used in relation to one or more steps in a method or process.

Further aspects and advantages of the present invention will become apparent from the ensuing description which is given by way of example only.

DISCLOSURE OF INVENTION

Formulation

According to one aspect of the present invention there is provided a formulation for parenteral administration which includes:

selenomethionine; and, at least one oil-based vehicle.

For the purposes of the specification, the term 'parenteral' refers to the form being taken into the body or administered in a manner other than through the digestive tract such as by subcutaneous or intramuscular injection.

For the purposes of the specification, selenomethionine chemical structure is of formula (I), representing the D and L enantiomer forms or their racemic mixture:

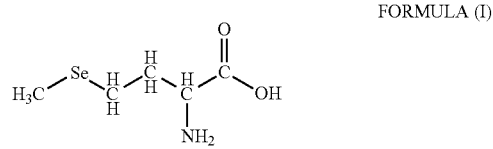

FORMULA (I)

Preferably, the selenomethionine is in micronised particulate form. More preferably, the selenomethionine form is a distribution of particle sizes of 0.1 to 10 µm.

Preferably, the concentration of selenomethionine in the formulation ranges from approximately 25 to 100 g/L. More preferably, the concentration of selenomethionine is approximately 50 g/L.

Preferably, the oil-based vehicle or vehicles are characterised by being non-allergenic, thin and flowing at room temperature, and slow to deteriorate by oxidation. In one preferred embodiment, the oil-based vehicle has a viscosity of approximately 50-100 mPa·sec @23° C. In preferred embodiments, the vehicle is vegetable oil. More preferably, the vehicle is selected from arachis oil, poppyseed oil and walnut oil. Most preferably, the vehicle is arachis (peanut) oil or similar oil with equivalent properties of viscosity and temperature stability.

Preferably, the formulation also includes a suspending agent. The aim of the suspending agent is to thicken the formulation sufficiently that, on shaking of a vessel of the formulation, the particles of selenomethionine remain suspended in the vehicle for long enough to allow the user to repeatedly withdraw formulation from a container and administer the formulation to animals.

In preferred embodiments, the suspending agent is beeswax, more preferably, white beeswax. It is the inventors' understanding that beeswax provides optimum suspension and flow characteristics for the formulation by thickening the mixture and therefore slowing the settling of particles of the selenomethionine out of solution. Preferably the beeswax is added in a concentration ranging from approximately 5 to 50 g/L. More preferably, the concentration may be approximately 15 g/L. It is the inventors' experience that this concentration range avoids the formulation becoming too thick at low temperature whilst still minimising settling of the suspension.

Preferably, the suspending agent is of a suitable pharmaceutical grade.

Preferably, sufficient suspending agent is added to result in a formulation with a density of approximately 0.92 g/ml when measured at 23° C.

Method of Administration

According to a further aspect of the present invention there is provided a method of elevating the level of selenium in an animal by parenteral administration of a formulation substantially as described above.

According to a further aspect of the present invention there is provided a method of meeting the selenium nutritional requirement for growth and health in a deficient animal by parenteral administration of a formulation substantially as described above.

According to a further aspect of the present invention there is provided a method of increasing the concentration of selenium in the milk and/or meat from that animal by parenteral administration of a formulation substantially as described above.

According to a further aspect of the present invention there is provided a method of increasing the concentration of selenium in the milk and/or meat from that animal by parenteral administration of repeated doses of a formulation substantially as described above.

Preferably, the repeated doses of the formulation are administered at varying intervals. More preferably, the subsequent dose(s) of the formulation are administered approximately 50 days after the administration of the first or preceding dose.

Preferably the formulation is administered to a ruminant animal. More preferably, the animal is a cow, goat or sheep.

Preferably, the formulation is administered by subcutaneous or intramuscular injection. On administration, the formulation forms a depot.

For the purposes of the specification, the term 'depot' refers to a reservoir of formulation that tends to stay at the administration site, releasing a sustained therapeutic amount of selenomethionine so that absorption occurs over a prolonged time period.

According to a further aspect of the present invention there is provided the use of a formulation substantially as described above wherein, on parenteral administration of a therapeutically effective quantity of the formulation, as either a single or repeated dosage, the selenium status of an animal (e.g. the concentration of selenium in blood) is increased by 6- to 25-fold for at least 95 days compared with animals that have not been treated. This blood status is safe and beneficial to the animal, and in the inventors' experience, is more than adequate to meet the animal's essential requirements for growth and health.

The inventors also found that the repeated administration of the formulation to dairy cows increased milk selenium levels as much as 27- to 54-fold in comparison to no treatment, and maintained concentrations at least 2-fold for at least 95 days. This enrichment is such that a 100 mL serving supplies up to 50% and up to 200% of the selenium RDI for adults and toddlers, respectively. Given this enrichment, dry milk powder made from the milk then processed into infant formula would not need to have any selenium added during powder processing as is current manufacturing practice.

The peak selenium concentration in milk occurs during the period of approximately 7 to 15 days after administration, with levels remaining elevated compared to no treatment for at least 95 days post-administration. This rate of release of the depot was unexpected and surprising to the inventors. It provides a useful time frame that allows treated cows to briefly produce very highly-enriched milk (which can be collected as an added-value specialty milk) then return to normal production. In this way, the formulation provides a "switch" to turn milk selenium enrichment on and off.

Furthermore, repeated administration of the formulation to sheep also increases the concentration of selenium in the muscle meat of an animal by 5- to 13-fold compared with no treatment.

It is the inventors' experience that injection of the formulation exhibits a depot effect sufficient to allow a useful duration for the above mentioned responses in tissues (blood, milk and/or meat), but not so long that the treated animal needs to be withheld from further processing post-administration. It should be appreciated by those skilled in the art that effect on tissues may be titrated by dosing to control the amplitude and duration of the selenium response.

It is the inventors' experience that the relationship between selenium concentrations in whole blood or blood serum and milk or meat is proportional but not linear. The relationship varies with the selenium source used for animal supplementation, such that selenomethionine differs from barium selenate which differs from sodium selenate. In the inventors' experience, selenomethionine is the most efficient supplement for enriching milk or meat selenium content relative to blood selenium concentration[1].

[1] Knowles SO, Grace N D, Wurms K, Lee J. Significance of amount and form of dietary selenium on blood, milk, and casein selenium concentrations in grazing cows. Journal of Dairy Science 82:429-437, 1999.

It is envisaged by the inventors that chemical speciation of the "extra" selenium in milk and/or meat from treated animals will be in the forms of selenomethionine and selenocysteine with lesser amounts as free selenium ion and Se-methylselenocysteine. A spread of speciation of this nature would likely be advantageous for a consumer as these forms of selenium have good bioavailability and metabolic efficacy.

The milk and/or meat from treated animals is considered safe for human consumption by the Agricultural Compounds and Veterinary Medicines (ACVM) group of the New Zealand Food Safety Authority (NZFSA). Further, it is the inventors' experience that meat from treated lambs is not changed or diminished in flavour, odour and other organoleptic properties compared to untreated meat, as determined by a panel of trained taste evaluators and by a large survey of untrained consumer volunteers.

BRIEF DESCRIPTION OF DRAWINGS

Further aspects of the present invention will become apparent from the following description which is given by way of example only and with reference to the accompanying drawings in which.

BEST MODES FOR CARRYING OUT THE INVENTION

The composition of the present invention is now described in terms of four field trials in livestock animals that were completed to determine the effect of administration of the formulation on animal blood selenium status and on milk selenium concentration (Examples 1 and 4) or on meat selenium concentration (Examples 2 and 3).

EXAMPLE 1

Selenium Enriched Milk from Dairy Cows

A trial was completed on a total of 13 grazing dairy cows (6 treated and 7 untreated) to determine the effects over time of the selenomethionine formulation on blood and milk selenium levels. Animals were treated by parenteral subcutaneous administration of a formulation substantially as described above, at a dose rate of approximately 0.35 mg selenium/kg liveweight. Blood and milk samples were collected from the cows on days 1, 7, 17, 28, 45 and 83 post-administration, and analysed for total selenium concentration.

Figure 1:
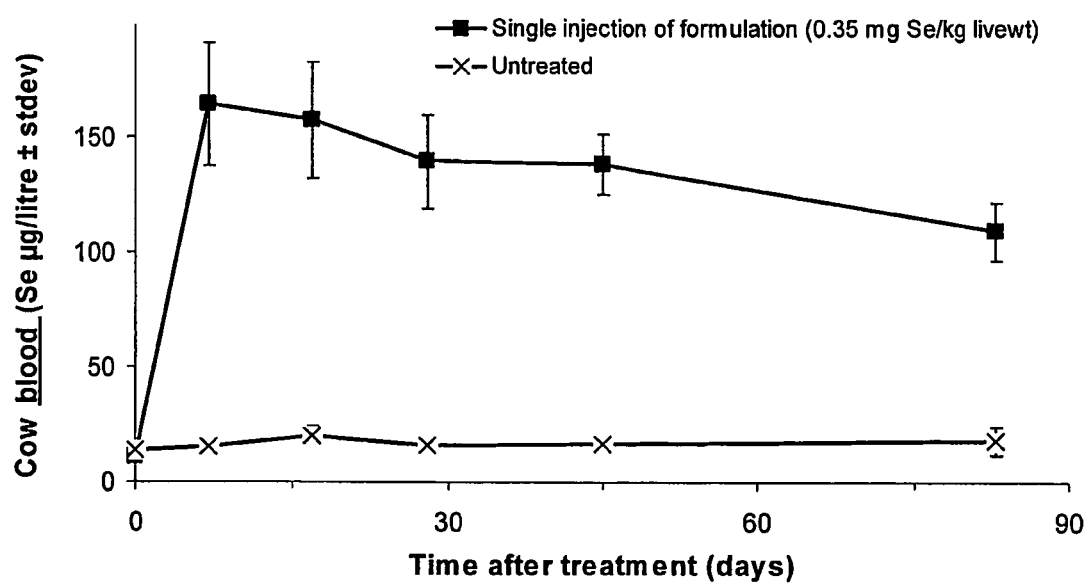
FIG. 1, shows a graph demonstrating over the duration of the field trial described in Example 1 the efficacy of the formulation to increase and maintain the selenium status of treated dairy cows as indicated by blood selenium concentration. n=about 6 per group.
Figure 2:
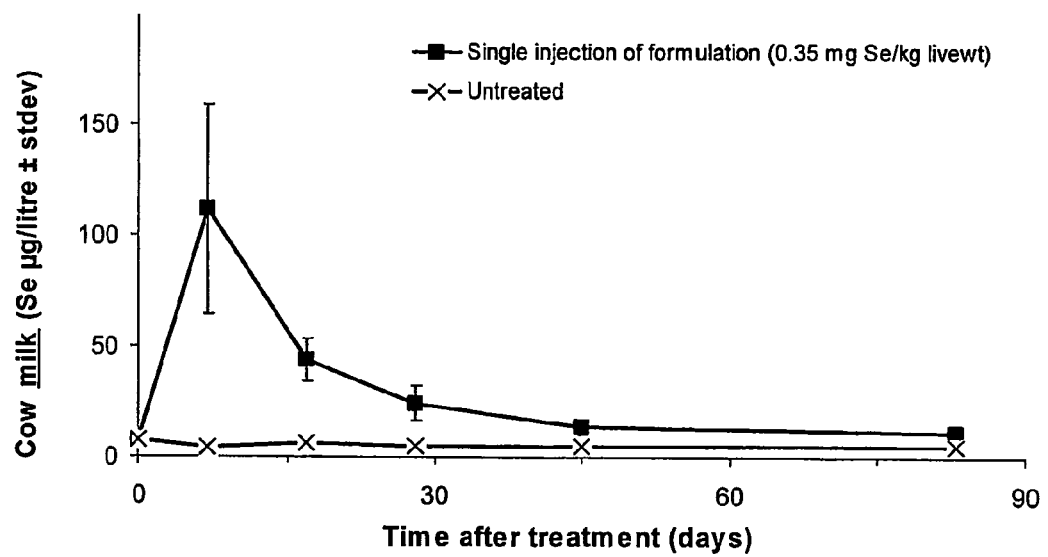
FIG. 2 shows a graph demonstrating over the duration of the field trial described in Example 1 the efficacy of the formulation to markedly increase the selenium concentration in fresh whole milk collected from dairy cows. n=about 6 per group.

The results as presented in FIG. 1 show a marked increase in mean blood selenium concentration of 6- to 11-fold over no treatment for at least 83 days, at which time measurements ceased. As shown in FIG. 2 milk selenium levels were significantly increased, with peak concentration of 28-fold over no treatment occurring approximately 7 days after administration, and levels remaining elevated for at least 83 days post-administration.

Clearly, a single injection of selenomethionine given to dairy cows increases not only the animal blood selenium concentration but also selenium levels in the milk from the animal, therefore demonstrating a useful transfer of selenium from blood to milk.

EXAMPLE 2

Selenium Enriched Meat from Lambs

A trial was completed on a grazing flock of 60 young lambs to determine the effects over time of the selenomethionine formulation on blood and muscle meat selenium levels. On day 1 of the trial, 20 lambs of about 4 weeks of age received a subcutaneous injection of the formulation substantially as described above, at a dose rate of approximately 0.8 mg selenium/kg liveweight. Twenty other lambs received an injection of a commercial preparation of barium selenate called Novartis Deposel®, at a dose rate of approximately 1.8 mg selenium/kg liveweight. Twenty additional lambs were untreated. Blood samples were collected from the lambs on days 1, 19, 40, 89 and 138 post-administration, and analysed for total selenium concentration and activity of glutathione peroxidase, a selenium-containing enzyme.

Muscle meat samples were collected by a "serial slaughter" scheme, in which a few animals from each treatment group were slaughtered at intervals up until the last day of the trial when all remaining animals in the groups were slaughtered. Thus muscle meat samples were collected from 2 animals per group on day 1, and from 6 animals per group on each of days 40, 89 and 138. Two different muscles per animal were analysed for selenium concentration. Those muscles were m. semitendinosus (eye of round) and m. triceps brachii (bolar).

Figure 3:
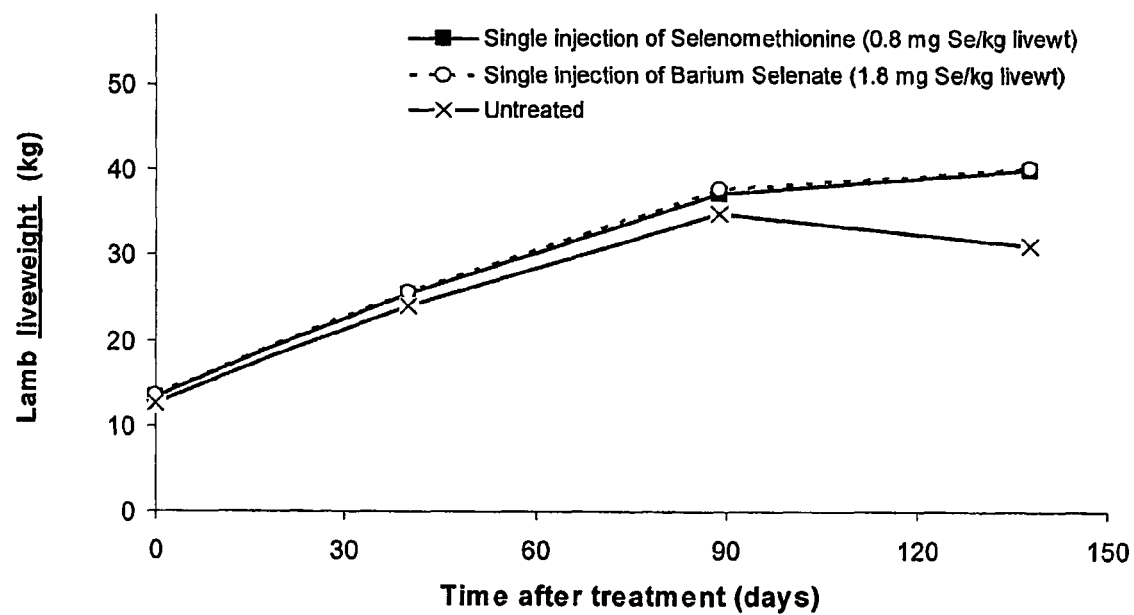
FIG. 3 shows a graph of efficacy of the formulation to meet the essential selenium nutritional requirement for growth and health in otherwise selenium-deficient lambs as indicated by animal liveweight over the duration of the field trial described in Example 2. n=20 per group.

The results as presented in FIG. 3 show that growth was impaired in untreated selenium-deficient lambs. Those animals did not grow to their full potential and lost weight as their health became compromised. In contrast, treatment with the selenomethionine formulation met the lambs' essential selenium requirements for growth and health. The efficacy of the formulation as an animal supplement was equivalent in this respect to Deposel®, a known and successful animal remedy based on barium selenate (an inorganic selenium salt).

Figure 4:
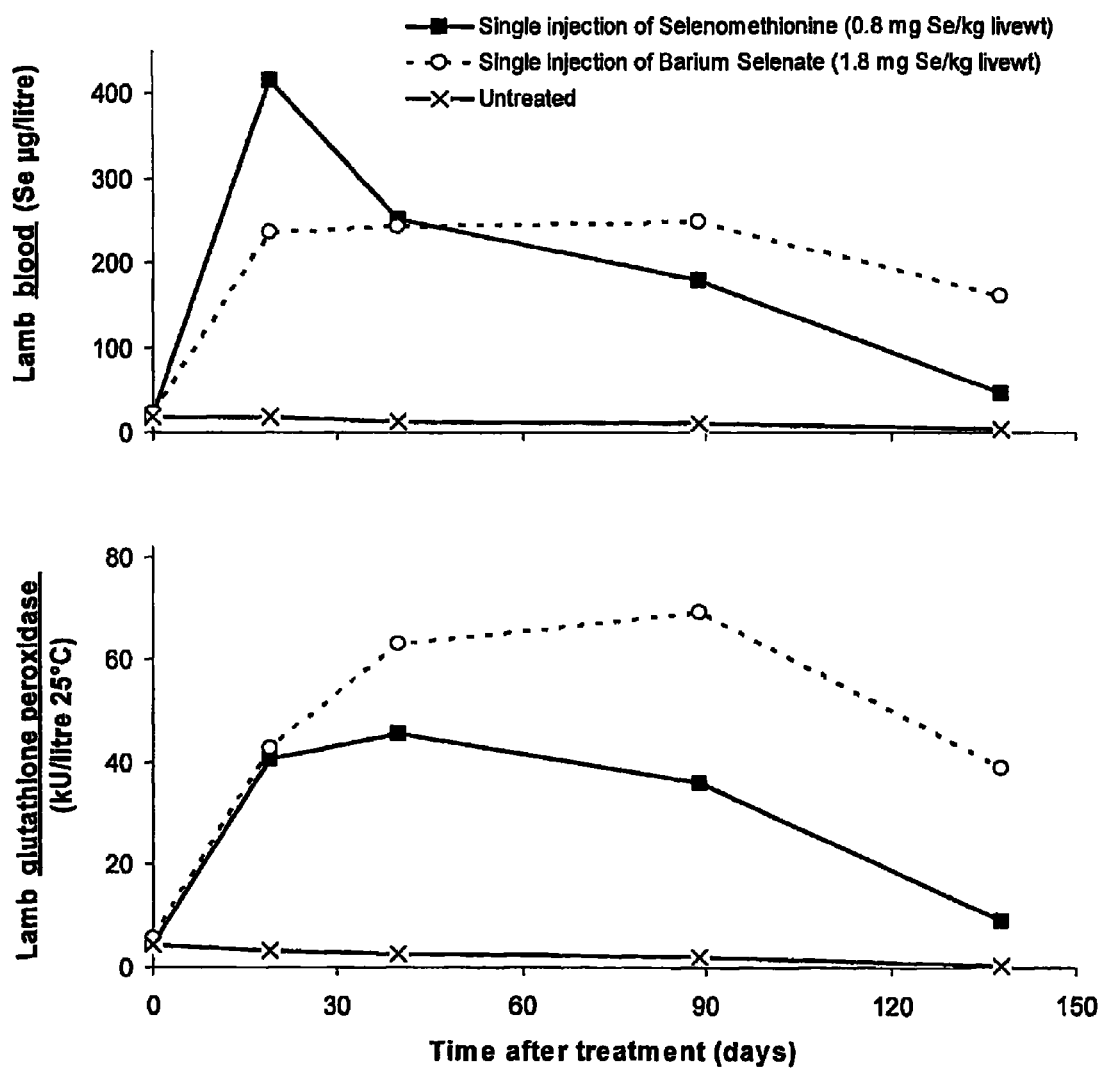
FIG. 4 shows a set of graphs demonstrating over the duration of the field trial described in Example 2 the efficacy of the formulation to increase and maintain the selenium status of treated lambs as indicated by blood selenium concentration (upper panel) and blood selenoprotein glutathione peroxidase activity (lower panel). n=20 per group.

The results in FIG. 4 (upper panel) show that treatment with either the selenomethionine formulation or Deposel® caused a marked increase in mean blood selenium concentration over no treatment for at least 138 days, at which time measurements ceased. In FIG. 4 (lower panel) an alternate index of animal selenium status, namely mean blood glutathione peroxidase activity, is also shown to be significantly elevated by treatment.

Figure 5:
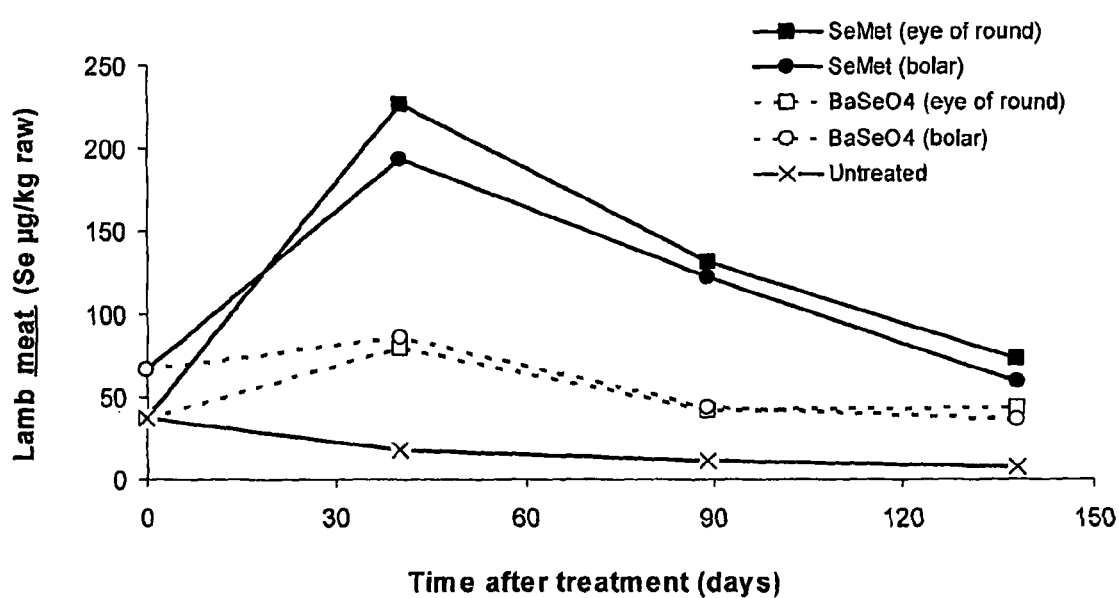
FIG. 5 shows a graph from the field trial described in Example 2 demonstrating the efficacy of the formulation to increase the selenium concentration in raw muscle meat from treated lambs. n=about 6 per group.

The results in FIG. 5 demonstrate how treatment with selenomethionine is much more efficient than barium selenate for enriching meat selenium concentration. Here a smaller dose administered on day 1 (0.8 mg selenium/kg liveweight as selenomethionine vs.1.8 mg selenium/kg liveweight as barium selenate) produced a larger increase in meat selenium. The increase peaked on day 40 (12-fold and 5-fold greater than no treatment). However this maximal selenium level occurred when the lambs were still small at just 25 kg. By day 89 when liveweight was 38 kg (an economically viable weight for slaughter) meat selenium concentration had fallen by 39%, due to dilution effects of muscle gained in 13 kg of growth. Note that abbreviations used in the legend of this figure are 'SeMet' for selenomethionine, 'BaSeO4' for barium selenate, 'eye of round' for m. semitendinosus and 'bolar' for m. triceps brachii.

Clearly, a single injection of selenomethionine given to lambs increases not only the animal selenium status but also selenium levels in muscle meat of the animal, therefore demonstrating a useful transfer of selenium from blood to muscle tissue. The selenomethionine formulation gives a similar pharmacokinetic profile (as indicated by changes in blood selenium concentration over time) to that of barium selenate even though the dose (depot size) is smaller. To achieve maximum concentration of selenium in muscle meat, treatment with the formulation should occur early in animal life so that selenium can be endogenously incorporated into muscle tissue of the rapidly growing animal.

EXAMPLE 3

Selenium Enriched Meat from Lambs Using an Optimised Treatment Scheme

A trial was completed on a grazing flock of 30 young lambs to determine the effects over time of repeated treatments with the selenomethionine formulation on blood and muscle meat selenium levels. On day 1 of the trial, 16 lambs of about 5 weeks of age received a single subcutaneous injection of the formulation substantially as described above, at a dose rate of approximately 0.7 mg selenium/kg liveweight. Of those, 10 received a second injection of the formulation on day 54, at a dose rate of approximately 0.6 mg selenium/kg liveweight. Fourteen lambs were untreated throughout the trial.

Blood samples were collected from the lambs on days 1, 19, 54, 73 and 90 post-administration, and analysed for total selenium concentration (data not shown).

Muscle meat samples were collected by a curtailed "serial slaughter" scheme, in which a few animals from each treatment group were slaughtered pre-treatment at the start of the trial and all remaining animals in the groups were slaughtered at the end of the trial. Thus muscle meat samples were collected on day 1 from 5 untreated lambs. On day 95, samples were collected from the 9 remaining untreated lambs, from 6 single-injected lambs, and from 10 double-injected lambs. Two different muscles per animal were analysed for selenium concentration. Those muscles were m. semitendinosus (eye of round) and m. longissimus dorsi lumborum (striploin).

Figure 6:
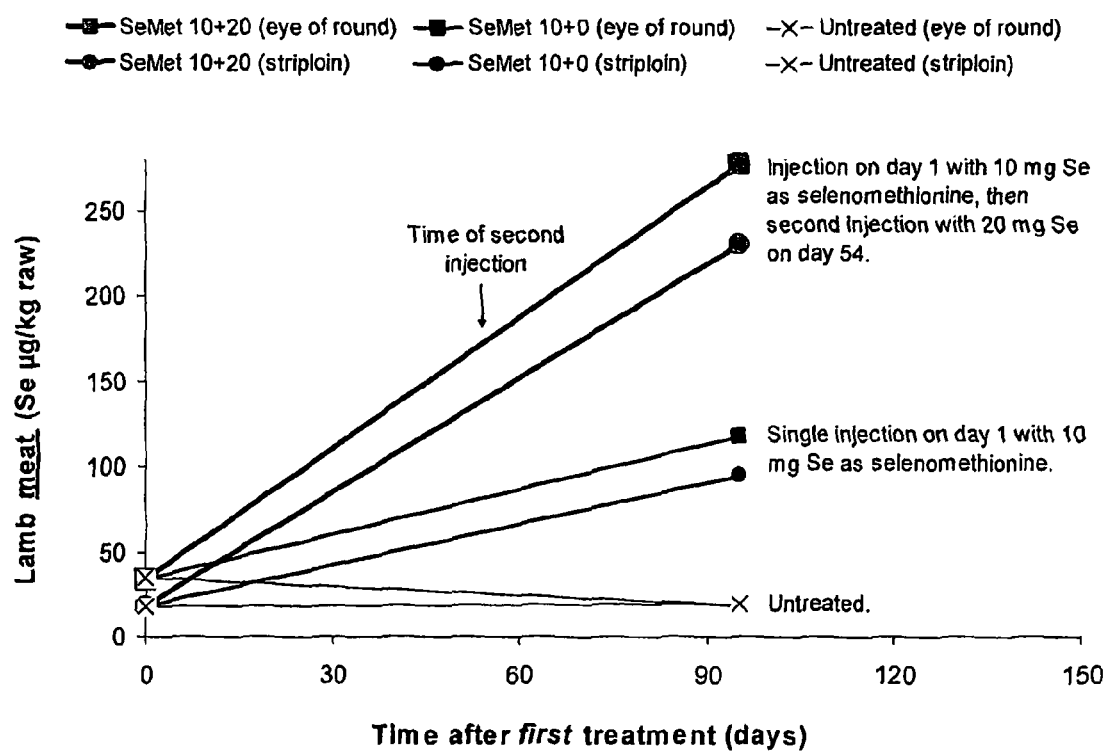
FIG. 6 shows a graph from the field trial described in Example 3 demonstrating the efficacy of the formulation to increase the selenium concentration in raw muscle meat from treated lambs, whereby administering a second injection of the formulation at 40 days prior to slaughter further increases the selenium effect. n=about 7 per group.

The results in FIG. 6 show how initial treatment with the selenomethionine formulation at a young age, followed by a second injection of the formulation about 40 days prior to slaughter, maintains high selenium concentration in the muscle meat as the lamb grows to an economically viable slaughter weight. Mean liveweight of the lambs slaughtered on day 95 was 44 kg (data not shown). On that day, the meat selenium concentration was 13-fold greater than no treatment. Note that abbreviations used in the legend of this figure are 'SeMet' for selenomethionine, '10+0' for single-injected lambs, '10+20' for double-injected lambs, 'eye of round' for m. semitendinosus, and 'striploin' for m. longissimus dorsi lumborum.

Figure 7:
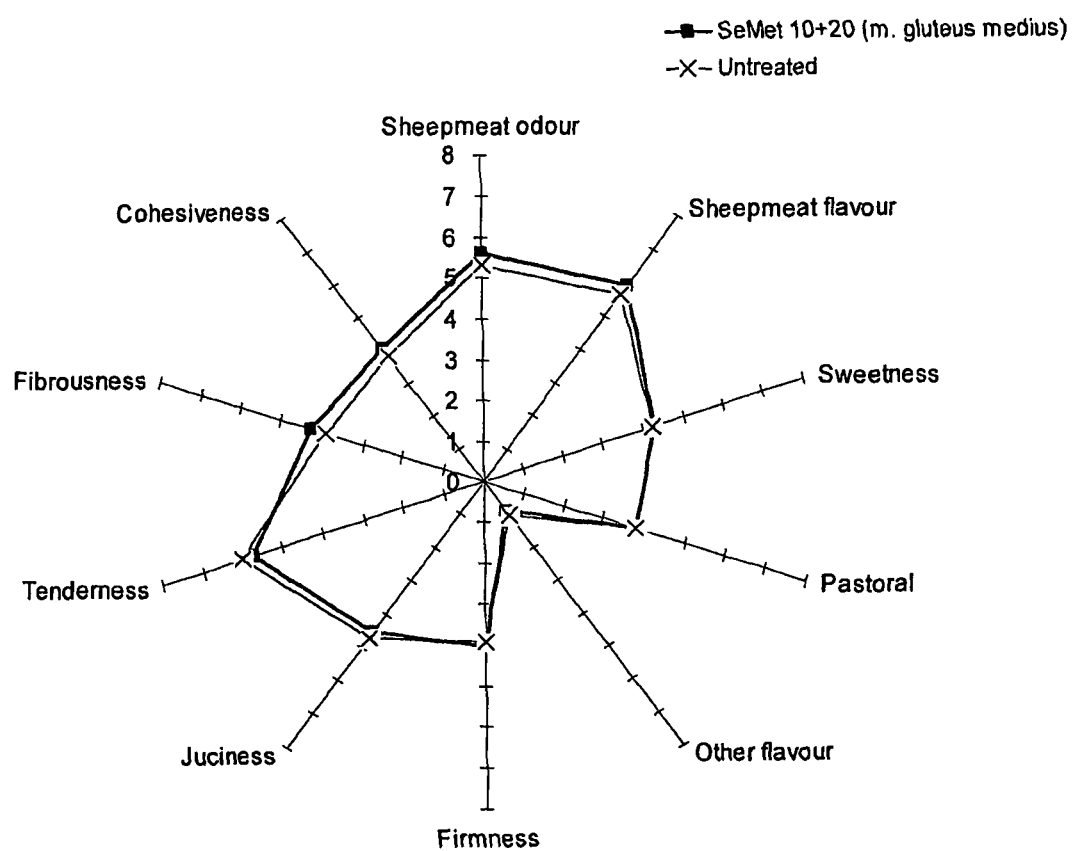
FIG. 7 shows a radar graph of organoleptic attributes of lamb meat from the field trial described in Example 3, demonstrating no significant effect of selenomethionine treatment on the taste and texture of selenium-enriched meat. n=6-10 per group.

The results in FIG. 7 show the mean responses of a nine-member panel of trained sensory evaluators. Under controlled conditions, these panellists tasted cooked meat from nine untreated and ten '10+20' double-injected lambs in order to compare each sample for aroma, flavour, tenderness, texture, and juiciness on an 8-point hedonic scale. Treatment of lambs with the selenomethionine formulation by the optimised method did not affect the eating quality or acceptability of the resulting selenium-enriched lamb meat.

EXAMPLE 4

Selenium Enriched Milk from Dairy Cows—Repeated Treatments

A trial was completed on a total of 40 dairy cows, that were randomly assigned to 4 groups of 10, to determine the effects of time of treatments, including repeated treatments with selenomethionine formulation on blood and milk selenium levels. The groups were divided into treatments consisting of (a) no treatment (Group CONTROL) or; (b) selenomethionine at a dose rate of 0.35 mg selenium/kg liveweight (Group LOW ONCE) or; (c) 0.35 mg selenium/kg liveweight as above, then a second similar injection on Day 49 (Group LOW REPEATED) or; (d) 0.70 mg selenium/kg liveweight, then a second similar injection on Day 49 (Group HIGH REPEATED). On day 0, each group (n=10 cows per group) received a single subcutaneous injection of their designated treatment. Blood and whole milk samples were collected from the cows prior to treatment at Days −9 and 0, and again during lactation at Days 5, 12, 26, 49, 54, 61, 76 and 95. Details and timing of animal samplings are summarised below in Table 1.

TABLE 1

| Trial Day | Action |
|---|---|
| −9 | Blood samples collected from the cows |
| −2 | Milk samples collected from the cows |
| 0 | 40 cows assigned into treatment groups |
|   | 40 cows treated with selenomethionine. |
|   | Serum only sampling of 40 cows. |
|   | Trial begins. |
| 5 | Blood sampling and milk collection from the cows |
| 6 | Pasture herbage samples collected |
| 12 | Blood sampling and milk collection from the cows |
| 26 | Blood sampling and milk collection from the cows |
| 34 | Pasture herbage samples collected |
| 49 | Blood sampling and milk collection from the cows, then 20 cows given 2nd treatment of selenomethionine. |

TABLE 1-continued

| Trial Day | Action |
|---|---|
| 54 (5*) | Blood sampling and milk collection from 40 cows |
| 61 (12*) | Blood sampling and milk collection from 20 cows |
| 76 (27*) | Blood sampling and milk collection from 20 cows |
| 95 (46*) | Blood sampling and milk collection from 40 cows |

*indicate the number of days relative to the 2$^{nd}$ treatment

Figure 8:
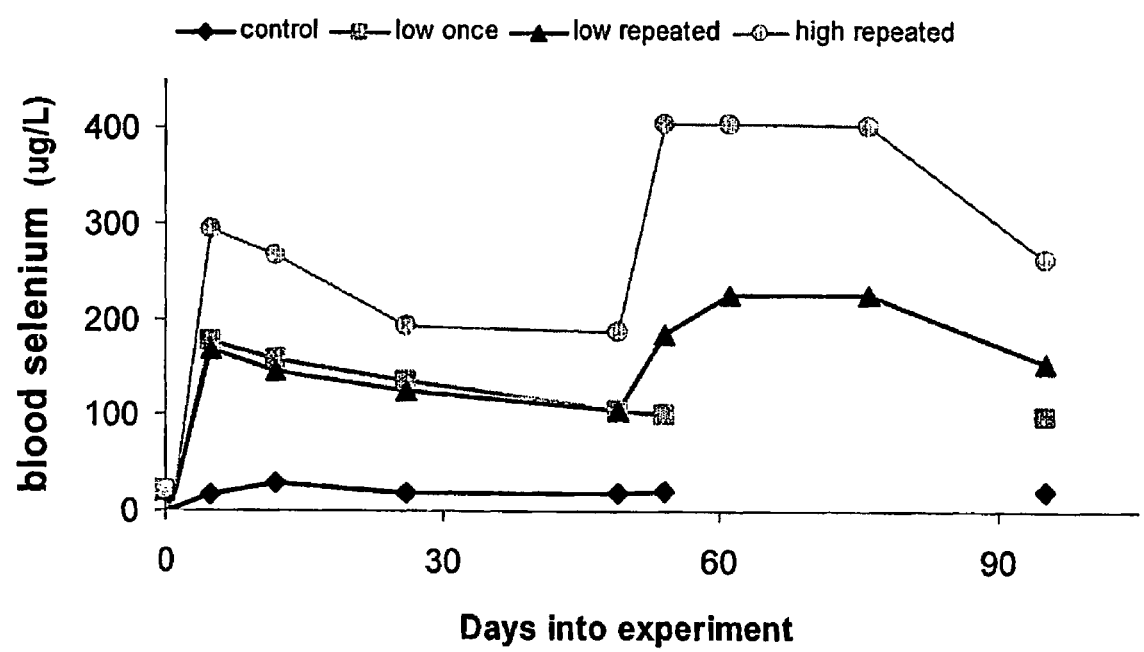
FIG. 8 shows a graph demonstrating over the duration of the field trial described in Example 4 the efficacy of the formulation to increase and maintain the selenium status of treated dairy cows as indicated by blood selenium concentration, by either one injection of the formulation or by one injection followed by another injection approximately 50 days from the administration of the first injection. n=10 per group.

The results as shown in FIG. 8 show that the blood selenium concentrations increased 10- to 18-fold on Day 5 for both the single and first injection of the repeat groups, in comparison to the control group. The increase of blood selenium levels for the repeated treatments increased 9- to 20-fold on Day 54 in comparison to the controls. Response to the second treatment was slightly less than the response to the first, but their combined effects were cumulative. Overall, blood selenium concentrations were maintained very high for the duration of the study, which was approximately 95 days.

Figure 9:
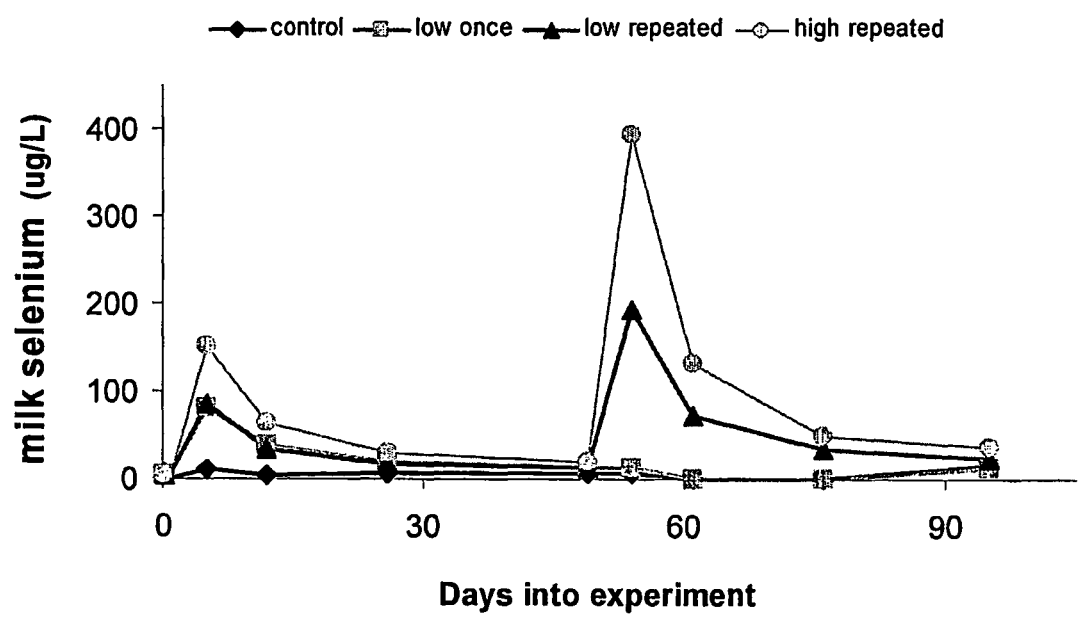
FIG. 9 shows a graph demonstrating over the duration of the field trial described in Example 4 the efficacy of the formulation to increase the selenium concentration in fresh whole milk collected from dairy cows, by the administration of either one injection of the formulation or by one injection followed by another injection approximately 50 days from the administration of the first injection. n=10 per group.

The results shown in FIG. 9 showed that selenium concentration in whole milk peaked 8- to 14-fold in comparison to the control on Day 5 at the first sampling period. The repeated treatments caused milk selenium concentration to peak 27- to 54-fold greater than controls on Day 54. Milk selenium concentrations were maintained at about twice in comparison to the control for at least 95 days. Response to the second treatment was slightly less than the response to the first, but their combined effects were cumulative.

The inventors note that the milk peak concentration following repeated dose represents exceptionally effective extraction. It is hypothesised by the inventors that the mammary gland extraction processes were primed by the first dose, resulting in a greater proportion of the second selenomethionine injection being delivered to milk.

From the above examples, it should be appreciated that there is provided a formulation which is able to increase and sustain for a period of time levels of selenium within the blood, milk and/or meat of an animal. Also provided are suitable methods for the administration and preparation of the formulation.

Aspects of the present invention have been described by way of example only and it should be appreciated that modifications and additions may be made thereto without departing from the scope thereof.

What we claim is:

1. A veterinary formulation for injectable administration which includes:
   selenomethionine; and,
   at least one oil-based vehicle;
   wherein the concentration of selenomethionine ranges from 25 to 100 g/L;
   wherein the oil-based vehicle comprises arachis oil or an oil that has equivalent properties of viscosity and temperature stability to arachis oil; and
   wherein the formulation is suitable for subcutaneous or intramuscular injection and forms a depot on administration.

2. The formulation as claimed in claim 1, wherein the selenomethionine chemical structure has the following formula, representing the D and L enantiomer forms or their racemic mixture:

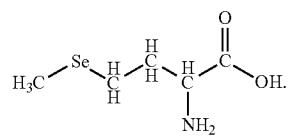

3. The formulation as claimed in claim 1, wherein the selenomethionine is in micronised particulate form.

4. The formulation as claimed in claim 1, wherein the selenomethionine form is a distribution of particle sizes from approximately 0.1 to 10 μm.

5. The formulation as claimed in claim 1, wherein the oil-based vehicle or vehicles are characterised by being non-allergenic, thin and flowing at room temperature and slow to deteriorate by oxidation.

6. A formulation as claimed in claim 1, wherein the formulation also includes a suspending agent.

7. A formulation as claimed in claim 6, wherein the suspending agent is beeswax.

8. A formulation as claimed in claim 7, wherein the beeswax is white beeswax.

9. A formulation as claimed in claim 6, wherein the beeswax is added in a concentration ranging from approximately 5 to 50 g/L.

10. A formulation as claimed in claim 7, wherein the beeswax is added in a concentration is approximately 15 g/L.

11. A formulation as claimed in claim 6, wherein the suspending agent is of a pharmaceutical grade.

12. A formulation as claimed in claim 6, wherein sufficient suspending agent is added to the formulation so that the formulation has a resulting density of approximately 0.92 g/ml when measured at 23° C.

* * * * *